United States Patent
Chen et al.

(10) Patent No.: US 9,518,238 B2
(45) Date of Patent: Dec. 13, 2016

(54) TRANSESTERIFICATION CATALYST AND METHOD FOR PRODUCING BIODIESEL FUEL USING TRANSESTERIFICATION CATALYST

(71) Applicant: National Institute of Advanced Industrial Science and Technology, Tokyo (JP)

(72) Inventors: Shih-Yuan Chen, Ibaraki (JP); Makoto Toba, Ibaraki (JP); Yuji Yoshimura, Ibaraki (JP); Takehisa Mochizuki, Ibaraki (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 0 days.

(21) Appl. No.: 14/763,534

(22) PCT Filed: Jul. 26, 2013

(86) PCT No.: PCT/JP2013/070335
§ 371 (c)(1),
(2) Date: Jul. 27, 2015

(87) PCT Pub. No.: WO2014/115356
PCT Pub. Date: Jul. 31, 2014

(65) Prior Publication Data
US 2015/0361365 A1    Dec. 17, 2015

(30) Foreign Application Priority Data

Jan. 28, 2013 (JP) ................................. 2013-013720

(51) Int. Cl.
*C07C 67/02* (2006.01)
*C10L 1/02* (2006.01)
(Continued)

(52) U.S. Cl.
CPC .............. *C10L 1/026* (2013.01); *B01J 21/063* (2013.01); *B01J 29/89* (2013.01); *B01J 35/10* (2013.01);
(Continued)

(58) Field of Classification Search
CPC ........... B01J 21/063; B01J 29/89; B01J 35/10; C10L 2200/0476
See application file for complete search history.

(56) References Cited

U.S. PATENT DOCUMENTS

| 5,508,457 A | 4/1996 | Bayense et al. |
| 5,565,605 A * | 10/1996 | Tsuneki ................. C07C 68/06 560/109 |

(Continued)

FOREIGN PATENT DOCUMENTS

| CN | 103012127 | 4/2013 |
| JP | 11-140026 | 5/1999 |

(Continued)

OTHER PUBLICATIONS

JP200500398 (A), Oku Tomoharu et al., Method for producing fatty acid alkyl ester and/or glycerol, English Translation, 24 pages.*

(Continued)

*Primary Examiner* — Yate K Cutliff
(74) *Attorney, Agent, or Firm* — Carmody Torrance Sandak & Hennessey LLP

(57) ABSTRACT

To provide a catalyst for production of a biodiesel fuel, which is capable of producing a biodiesel fuel with high selectivity, at a high yield, and at a low cost even in the presence of a water content and a free fatty acid, and a biodiesel fuel production method using the catalyst. Use of a titanium-containing mesoporous silica containing Ti and Si as skeleton constituent elements and having a pore diameter of 5 nm or greater as a transesterification catalyst (Continued)

enables a biodiesel fuel to be produced with high selectivity at a high yield through transesterification between an oil and an alcohol.

6 Claims, 6 Drawing Sheets

(51) Int. Cl.

| | | |
|---|---|---|
| *C10L 1/188* | (2006.01) | |
| *B01J 29/89* | (2006.01) | |
| *B01J 35/10* | (2006.01) | |
| *C07C 67/03* | (2006.01) | |
| *C01B 37/00* | (2006.01) | |
| *B01J 21/06* | (2006.01) | |

(52) U.S. Cl.
CPC ............. *C01B 37/005* (2013.01); *C07C 67/02* (2013.01); *C07C 67/03* (2013.01); *C10L 1/1881* (2013.01); *C10L 2200/0476* (2013.01); *C10L 2270/026* (2013.01); *Y02E 50/13* (2013.01)

(56) References Cited

U.S. PATENT DOCUMENTS

| | | | |
|---|---|---|---|
| 5,663,480 A | 9/1997 | Tsuneki et al. | |
| 5,908,946 A | 6/1999 | Stern et al. | |
| 2007/0167642 A1* | 7/2007 | Oku | B01J 23/20 554/174 |
| 2009/0118116 A1* | 5/2009 | Yamashita | B01J 23/24 502/74 |
| 2012/0029218 A1 | 2/2012 | Kim et al. | |

FOREIGN PATENT DOCUMENTS

| | | |
|---|---|---|
| JP | 2005-126346 | 5/2005 |
| JP | 2006-151798 | 6/2006 |
| WO | 2005/021697 | 3/2005 |
| WO | 2006/094986 | 9/2006 |

OTHER PUBLICATIONS

JPH0892166 (A), Isuneki Hideaki et I., Production f aromatic carbonic acid ester and catalyst used therefor, English Translation, 12 pages.*

JPH11140026 (A), Onuki Masamichi et al., Production of carboxylic acid esters, English Translation 13 pages.*

Chen, Y et al., Direct systneshs, characterizatin and catalytic activity of titanium-substituted SBA-15 mesoporous molecular sieves, 2004, Applied Catalyst A: General Chemistry, vol. 273, pp. 184-191.*

Chen, S-Y, et al., Effect f calcination on the structure and catalytic activites of titanium incorporated SBA-15, 2011, Journal of Materials Chemistry, vol. 21, pp. 2255-2265.*

Lee, D-W., et al., Synthesis fo bimodal mesoporous titania with high thermal stability via replicatin of citric acid-templated mesoporous silica, 2007, Chemistry of Materials, vol. 19, pp. 947-941.*

Berube, F., et al., Controlled postgrafting of titanium chelates for improved synthesis of TiSBA-15 Epoxidation Catalyst, 2010, Chemistry of Materials, vol. 2, pp. 1988-2000.*

Wu P, et al., Postsynthesis, characterization, and catalytic properties in alkene epoxidatin of hydrothermally stable mesoporous Ti-SBA-15, 2002, Chem Mater, vol. 14, No. 4, pp. 1657-1664.*

Kouzu, M. et al., Development of Biodiesel Production Technology from Waste Cooking Oil with Calcium Oxide as Solid Base Catalyst, Journal of the Japan Petroleum Institute, vol. 50 (2), 2007, pp. 79-86.

Srinivas, D. et al., Transesterifications Over Titanosilicate Molecular Sieves, Catalysis Today, vol. 96, 2004, pp. 127-133.

Chen, Y. et al., Direct Systhesis, Characterization and Catalytic Activity of Titanium-Substituted SBA-15 Mesoporous Molecular Sieves, Applied Catalysis, vol. 273, 2004, pp. 185-191.

Chen, S-Y et al., Effect of Calcination on the Structure and Catalytic Activities of Titanium Incorporated SBA-15, J. Materials Chemistry, vol. 21, 2011, pp. 2255-2265.

Zhao, H-L et al., One-Step Synthesis of Metal-Doped Mesoporous MCM-41 Materials and Their Application in Esterification Catalysis, Acta Physico-Chimica Sinica, vol. 27 (2), 2011, pp. 499-504.

Srivastava, R., Synthesis of Polycarbonate Precursors Over Titanosilicate Molecular Sieves, Catalysis Letters, vol. 91, Nos. 1-2, Nov. 2003, pp. 133-139.

Ryoo, H.I., Direct Synthesis of Sulfonated Mesoporous $SiO_2$-$TiO_2$-$SO_3H$ Materials as Solid Acid Catalysts, Journal of Materials Chemistry, vol. 20, 2010, pp. 6419-6421.

Chen, S-Y et al., Ti-incorporated SBA-15 as an Efficient Solid Catalyst for the Production of High Quality Jatropha Biodiesel Fuel, International Symposium on Zeolites and MicroPorous Crystals, Hiroshima, Japan, Jul. 28, 2012 to Aug. 1, 2012.

Japanese Office Action dated May 17, 2016 issued for corresponding Japanese application.

* cited by examiner

Present invention

TRANSESTERIFICATION CATALYST AND METHOD FOR PRODUCING BIODIESEL FUEL USING TRANSESTERIFICATION CATALYST

TECHNICAL FIELD

The present invention relates to a transesterification catalyst, and a method for producing a biodiesel fuel using the transesterification catalyst.

BACKGROUND ART

Biodiesel fuels (BDF) made of a long-chain free fatty acid alkyl ester have begun to spread mainly in Europe, as an environmentally friendly alternative fuel to replace a light oil, because their raw materials are vegetable oil or animal oil, which are natural products. However, in order to be used as an automobile fuel and the like, biodiesel fuels must satisfy high quality standards provided by, for example, ASTM D6751-07b, EN14214:2003, JSI K2390:2008, and EEBS:2008, and must have a high stability.

Typically, a biodiesel fuel is obtained by adding an alcohol such as methanol to a plant-derived oil (fatty acid triglyceride) or the like, inducing transesterification using a homogeneous alkali catalyst such as sodium hydroxide to separate the materials into fatty acid alkyl ester and glycerin, distilling the fatty acid alkyl ester resulting from the separation to remove methanol, mixing the resultant with water to wash the residual homogeneous alkali catalyst, residual glycerin, and residual methanol, separating and removing these impurities dissolved in water together with the water layer, and then drying the resultant to remove the residual water content.

FIG. 1 shows an overview of the above process. However, it is not easy to produce a biodiesel fuel that satisfies fuel standards such as JIS K2390 through such a complicated production process.

Further, a homogeneous alkali catalyst corrodes the production equipment. Therefore, a special equipment is required. What is more, a large amount of waste water is produced through the production process, because sufficient water washing is required for residual metal removal. Furthermore, a lot of waste catalyst will be produced, because the homogeneous alkali catalyst is non-recyclable. Moreover, the homogeneous catalyst will be mixed in glycerin, which is the by-product, which adds to the refinement costs involved in utilization of glycerin.

Further, if a free fatty acid is contained in the raw material oil in a large amount, it reacts with the homogeneous alkali catalyst and produces a soap, which gives rise to a need for a previous step for removing the free fatty acid. Further, in order to prevent saponification and catalyst deactivation, it is necessary that the water content of the raw material be 0.3% or less. As seen above, through such a production method, the biodiesel fuels cannot compete with the light oil fuels in terms of economic efficiency and environmental hazardousness.

To overcome the problems described above, studies are conducted into biodiesel fuel production methods that use, instead of a homogeneous catalyst, a heterogeneous catalyst (solid catalyst) that can be used as it is, i.e., in its solid phase.

For example, studies using an alkali metal-carried catalyst (PTL 1), and an alkaline earth catalyst or a basic solid catalyst (PTL 2, NPL 1) are conducted. However, they have a problem that an active component such as calcium and lanthanum leaches into the produced oil at a high concentration, which tends to reduce the catalyst activity.

Further, according to a method using a zinc aluminate catalyst (PTL 3), high-temperature, high-pressure conditions are required for the reaction, and a residual glyceride level does not satisfy the standards mentioned above.

Furthermore, there is a report (NPL 2) that titania silica ($TiO_2/SiO_2$) that has gained wide publicity as an oxidation catalyst for epoxidation, etc., and Ti-MCM-41, which is Ti carried on a mesoporous material MCM-41, are relatively effective for transesterification between low-molecular-weight molecules and an alcohol, which leads to studies into biodiesel fuel production methods with catalysts using a mesoporous material and a microporous material.

However, it has been reported that with a titanosilicate TS-1, the active component tends to leach during the reaction (PTL 4), and that during a transesterification reaction using a titania-containing silica catalyst, the catalyst activity drops in the presence of a free fatty acid and water (PTL 5).

As seen above, various solid catalysts are being developed for production of biodiesel fuels, but all of these have problems. Particularly, with any of these solid catalysts, it is necessary to perform a step of removing a water content and a free fatty acid during transesterification for the sake of an efficient transesterification. Hence, the crucial problem of the homogeneous catalyst cannot have been solved with these solid catalysts.

Under these circumstances, it is requested to develop a solid catalyst with which transesterification of an oil, which is the main reaction, and esterification of a free fatty acid, which is an impurity, can be induced at the same time, and a biodiesel fuel can be produced at a high yield.

CITATION LIST

Patent Literature

| | |
|---|---|
| PTL 1 | Japanese Patent Application Laid-Open (JP-A) No. 2005-126346 |
| PTL 2 | United States Patent Application Publication No. 2012/029218 |
| PTL 3 | U.S. Pat. No. 5,908,946 |
| PTL 4 | International Publication No. WO 2005/021697 |
| PTL 5 | International Publication No. WO 2006/094986 |

Non-Patent Literature

| | |
|---|---|
| NPL 1 | J. Jpn. Petrol. Inst., 50, 79 (2007) |
| NPL 2 | Catalyst Today 96 127-133 (2004) |
| NPL 3 | Applied Catalysis A: General 273, 185 (2004) |
| NPL 4 | J. Materials Chemistry, 21, 2255, (2011) |

SUMMARY OF INVENTION

Technical Problem

In view of the problems of the existing technologies, an object of the present invention is to provide a biodiesel fuel production catalyst with which a biodiesel fuel can be produced with high selectivity, at a high yield, and at a low cost even in the presence of a water content and a free fatty acid, and a biodiesel fuel production method using this catalyst.

Solution to Problem

As the result of conducting studies for achieving the object described above, the present inventors have discovered that titanium-containing SBA-15 (Ti-SBA-15), which is known as an oxidation catalyst for epoxidation, etc. (see NPLs 3 and 4 identified above), is an excellent transesterification catalyst.

Further, the present inventors have synthesized various Ti-SBA-15 products having different Ti/Si molar ratios, different titanium contents, and different physical properties such as pore diameter, and examined transesterification between an oil and an alcohol with each of these products. As a result, the present inventors have discovered that not only is the yield of transesterification between an alcohol and triglyceride high, but also the activity of transesterification does not drop even in the presence of a water content and a free fatty acid with an optimally designed Ti-SBA-15, which is hence particularly useful for transesterification between an oil and an alcohol. Furthermore, the present inventors have discovered an efficient biodiesel fuel production method using this catalyst, and come to complete the present invention.

That is, the following inventions are provided.

[1] A transesterification catalyst, including:
a titanium-containing mesoporous silica including Ti and Si as skeleton constituent elements and having a pore diameter of 5 nm or greater.

[2] The transesterification catalyst according to [1],
wherein the titanium-containing mesoporous silica is SBA-15.

[3] The transesterification catalyst according to [2],
wherein the catalyst has a pore diameter of from 6.5 nm to 8 nm.

[4] The transesterification catalyst according to [1],
wherein the titanium-containing mesoporous silica has a mesostructured cellular form (MCF).

[5] The transesterification catalyst according to [4],
wherein the catalyst has a pore diameter of from 15 nm to 40 nm.

[6] The transesterification catalyst according to any one of [1] to [5],
wherein the mesoporous silica has a Ti/Si molar ratio of from 0.03 to 0.07.

[7] The transesterification catalyst according to any one of [1] to [6],
wherein the catalyst is for production of a biodiesel fuel through transesterification between an oil and an alcohol.

[8] A biodiesel fuel production method, including:
obtaining a fatty acid alkyl ester through transesterification between an oil and an alcohol in the presence of the transesterification catalyst according to any one of [1] to [7].

Advantageous Effects of Invention

According to the present invention, it is possible to induce transesterification efficiently with a solid catalyst containing a titanium-containing mesoporous silica. Particularly, it is possible to produce a biodiesel fuel efficiently through transesterification of an oil and an alcohol. With the catalyst of the present invention, transesterification between triglyceride and a short-chain alcohol is achieved at a high yield, and the reaction efficiency is not lowered even if a water content is contained in the reactants in an amount of about 10%. Furthermore, a free fatty acid that is present in an oil as an accessory component and has been a reaction inhibiting component in the conventional technologies can be esterified at the same time, which leads to a high biodiesel fuel yield. According to the production method of the present invention, it is possible to produce a biodiesel fuel that satisfies a fuel standard such as JIS K2390, and contains a fatty acid methyl ester in an amount of 96.5% by mass or greater, and total glycerin, monoglyceride, diglyceride, triglyceride, and free glycerin in amounts of 0.25% by mass or lower, 0.2% by mass or lower, 0.2% by mass or lower, 0.8% by mass or lower, and 0.02% by mass or lower, respectively.

According to the present invention, a one-stage biodiesel fuel production method that is capable of simultaneous esterification and transesterification with a solid catalyst can be achieved as shown in FIG. 2, and the catalyst of the present invention is recyclable with no discharging of a waste catalyst or polluted water, can simplify the process, and provides a high economic efficiency and an environmentally friendly technology.

DESCRIPTION OF EMBODIMENTS

A transesterification catalyst of the present invention is made of a titanium-containing mesoporous silica containing Ti and Si as skeleton constituent elements and having a pore diameter of 5 nm or greater. A biodiesel fuel production method of the present invention produces a biodiesel fuel from an oil by one stage through a transesterification reaction using the transesterification catalyst.

The present invention will be described in detail below.

Figure 1:
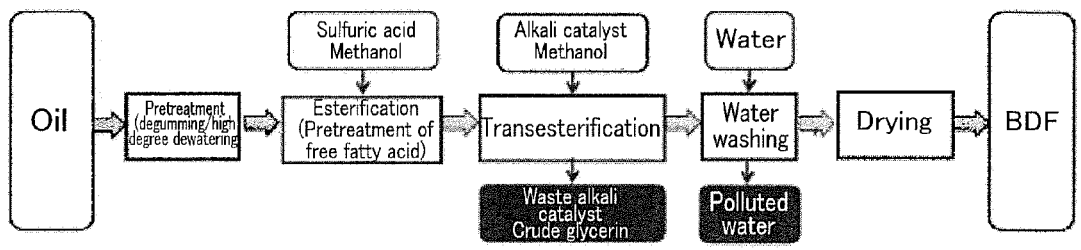
FIG. 1 is a diagram showing an overview of a conventional biodiesel fuel production process.
Figure 2:
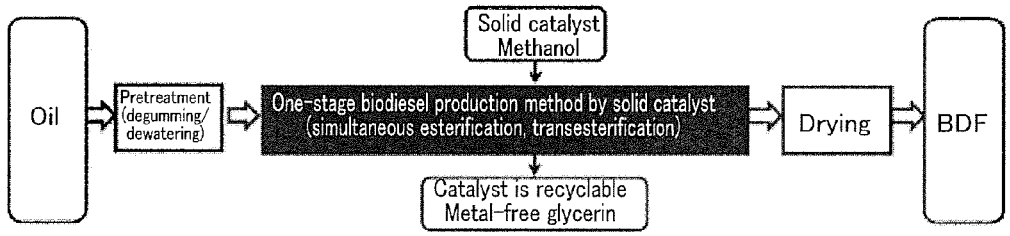
FIG. 2 is a diagram showing an overview of a biodiesel fuel production process of the present invention.

FIG. 2 is a diagram showing an overview of a biodiesel fuel production process of the present invention.

In the present invention, transesterification refers to a reaction in which an alcohol-derived substituent is interchanged through a reaction between an ester and an alcohol. In the present invention, it particularly refers to a reaction in which an alcohol acts on fatty acid triglyceride, which is the main component of a raw material oil, and on diglyceride or monoglyceride or both thereof, so that they may be transformed into an ester between the alcohol and a fatty acid, and into free glycerin.

The transesterification catalyst of the present invention is a titanium-containing mesoporous silica catalyst having a mesoporous structure. Being mesoporous means having a plurality of pores having a diameter of from 2 nm to 50 nm.

A mesoporous silica refers to a substance made of a silicon dioxide (silica) and having uniform pores (mesopores).

Examples of types of the mesoporous silica include M41S, MSU, FSM, MCM-41, and SBA. In the present invention, a mesoporous silica having a pore diameter of 5 nm or greater is used because an oil, which is a reactive substrate, has a large molecular size.

In the present invention, SBA-15 can be used favorably as the mesoporous silica having a pore diameter of 5 nm or greater, because its structure is stable.

In the present invention, an irregular mesostructured cellular form (MCF) can also be used favorably as the mesoporous silica having a pore diameter of 5 nm or greater. A mesostructured material refers to a material having mesopores obtained by forming a silica layer at the interface between an organic solvent that forms spherical liquid droplets in an aqueous solution and the aqueous solution, and removing the solvent.

The structural condition of the catalyst is not particularly limited, but an amorphous (non-crystalline) structure is preferred to a crystalline structure.

The titanium-containing mesoporous catalyst used in the present invention contains Ti and Si as structural skeleton constituent elements. The Ti/Si molar ratio is preferably from 0.01 to 0.1, and most preferably from 0.03 to 0.07.

The pore diameter of a titanium mesoporous silica catalyst based on SBA-15 (Ti-SBA-15) used in the present invention is preferably from 5 nm to 50 nm, more preferably from 5 nm to 10 nm, and yet more preferably from 6.5 nm to 8 nm.

The pore diameter of Ti-SBA-15 can be adjusted by increasing or decreasing the Ti/Si molar ratio.

The pores of SBA-15 are tubular, whereas the pores of a MCF structure are sponge-like and irregular. The pore diameter of a titanium-containing mesoporous silica catalyst having a MCF structure is preferably from 10 nm to 50 nm, and particularly preferably from 15 nm to 40 nm.

The pore diameter of the catalyst having the MCF structure can be adjusted by increasing or decreasing the molar ratio between trimethyl benzene and P123 added to a reaction liquid.

A method for producing a mesoporous silica is not particularly limited. Examples thereof include a method of performing a reaction step of depositing a silica through a reaction between a silicon alkoxide and an acid by two stages with extremely strict adjustment of the acid concentration in each stage, to thereby obtain a thin film-like mesoporous silica, and a method of mixing a surfactant and silicate soda and obtaining a mesoporous silica from a composite material of the surfactant and a silica.

In the present invention, a method for producing a titanium-containing mesoporous silica is not particularly limited. Examples thereof include a method of producing the same by using a block copolymer such as a nonionic amphiphilic polyalkylene oxide as a pore-forming agent (surfactant), ethyl orthosilicate as a silica source, titanium oxychloride as a titanium source, and a common salt as a structure regulating agent.

More specifically, first, titanium tetraisopropoxide is added to a concentrated hydrochloric acid, to synthesize a titanium oxychloride precursor. Next, a triblock copolymer (product name: PLURONIC P123), which is a nonionic surfactant containing PEO (polyethylene oxide), a common salt, and ethyl orthosilicate (TEOS: tetraethyl orthosilicate) are put into the same vessel, and hydrolyzed with distilled water or a hydrochloric acid. The titanium oxychloride precursor prepared above is added to the hydrolysis product, to thereby obtain a reaction solution. A resulting precipitate is washed with water, and then burned in a furnace, to thereby obtain a titanium-containing mesoporous silica.

The molar ratio of titanium tetraisopropoxide to the concentrated hydrochloric acid during the synthesis of the titanium oxychloride precursor is preferably from 0.5 to 50, and more preferably from 1.5 to 30. The concentration of the hydrochloric acid used for the synthesis of the hydrolysis product is preferably from 0.1 M to 1.0 M. However, the synthesis may be performed without a hydrochloric acid but with distilled water.

As the reaction progresses in the reaction solution, a regularly structured precipitate is formed by the surfactant molecules that are aggregated into columnar shapes being surrounded by silica as if the columnar shapes were a mold. Trimethyl benzene is further added to the reaction solution in order to obtain a mesoporous silica having an irregular mesostructured form.

When the catalyst has a regular structure, the pore diameter thereof is preferably from 6.5 nm to 8 nm. When the catalyst has an irregular mesostructured cellular form (MCF), the pore diameter thereof is preferably from 15 nm to 40 nm.

The Ti/Si molar ratio can be adjusted by changing the ratio between the triblock copolymer and ethyl orthosilicate used in the synthesis reaction. A Ti loading, as an equivalent loading of titania ($TiO_2$) to the catalyst, is preferably from 0.1% by weight to 10% by weight, and more preferably from 0.7% by weight to 8.1% by weight. A P123/TEOS molar ratio is preferably from 0.0087 to 0.022, and a NaCl/TEOS molar ratio is preferably in the range of from 0 to 6.

A preferable gel composition (molar ratio) of the present invention is P123:silicon:titanium:HCl:NaCl:water=0.013: 1:0.01 to 0.10:0.025 to 0.25:1:220.

The precipitate may be burned in order to obtain a more stable catalyst activity. The burning temperature is preferably 1,000° C. or lower, and particularly preferably from 500° C. to 800° C.

In the present invention, examples of an alcohol include methanol, ethanol, n-propanol, isopropanol, n-butanol, isobutanol, sec-butanol, and tert-butanol. Further examples include a branched or longer-chain alcohol, or as the case may be, a longer-chain and likewise branched alcohol, such as amyl alcohol, tert-amyl alcohol, n-hexanol, and 2-ethyl hexanol. Use of methanol and ethanol is preferable. In the method of the present invention, the above alcohols may be used alone or as a mixture.

In the present invention, an oil as a raw material of a biodiesel fuel refers to a natural oil used in foods, cosmetics, medical drugs, etc. Such an oil is a mixture containing fatty acid triglyceride as a main component, and diglyceride or monoglyceride or both thereof as accessory components, and can be transformed through transesterification to a fatty acid alkyl ester, which is the main component of a biodiesel fuel. Specific examples of an oil include a vegetable oil such as canola oil, sesame oil, jatropha oil, soy oil, corn oil, sunflower oil, palm oil, cottonseed oil, rice oil, palm oil, and safflower oil, an animal oil such as beef fat, lard, chicken fat, and fish oil, and a waste oil produced from these.

For transesterification between an oil and an alcohol, it is preferable that the molar ratio between methanol and an oil be larger, and be 100 or greater.

The transesterification reaction of the present invention may be performed under nitrogen pressurized at 0 bar to 40 bar, but pressurization is not particularly indispensable. The reaction temperature is preferably from 150° C. to 200° C., and the reaction time is preferably from 1 to 6 hours.

In the transesterification reaction of the present invention, it is preferable to remove a water content in the oil. However, as long as the water content is 10% or less, it is possible to induce transesterification at a high yield without removing water.

A free fatty acid may be removed, but removal is not particularly necessary to make it possible to induce transesterification.

The catalyst used in the present invention can be recovered and recycled. It is preferable to use a recycled catalyst that has been subjected to filtering, washing with an appropriate amount of acetone, drying at 30° C. to 50° C. for one night, and burning in air at 500° C. for 3 hours.

EXAMPLES

The present invention will be described below based on Examples. The present invention is not limited to these Examples.

Example 1

Preparation and Physical Property Analysis of Catalysts A to E (1) Preparation of Titanium Precursor While being stirred vigorously, 14.8 g (0.052 mol) of titanium tetraisopropoxide (TTIP) was added slowly to a 12.7 g (0.13 mol) of a concentrated hydrochloric acid (12 M) in a 50-mL beaker at 0° C. At the time, the HCl/TTIP molar ratio was maintained at 2.5. A titanium oxychloride precursor obtained according to this preparation method was a transparent yellow solution, in which no precipitate was observed at all.

(2) Preparation of Catalyst

In a 250-mL polypropylene-made bottle, 3 g of a triblock copolymer PLURONIC P123 (manufactured by Sigma-Aldrich Co., LLC., Mn=5800) and 2.36 g of a common salt were dissolved in 160 g of distilled water at 35° C. to 40° C. 8.4 g of ethyl orthosilicate (TEOS) was added to the resulting solution, stirred for 4 hours, and hydrolyzed in advance. Then, 0.213 g to 2.13 g of titanium oxychloride (from 1 mol % to 10 mol % relative to silicon) prepared in (1) was added thereto. At the time, the composition of the gel was P123:silicon:titanium:HCl:NaCl:water=0.013:1:0.01 to 0.10:0.025 to 0.25:1:220. The polypropylene-made bottle was sealed hermetically, stirred at 35° C. for 24 hours, and then subjected to a hydrothermal treatment by being kept stationary at 100° C. for 24 hours. A resulting white precipitate was filtered, washed with 500 mL of distilled water, and then dried at 100° C. for one night. The resultant was burned at 500° C. for 3 hours in air (at a temperature ramping rate of 1° C./minute) in order for P123 contained in the catalyst to be removed. According to the method described above, catalysts A, B, C, D, and E (with titanium contents of 1, 3, 5, 7, and 10 mol %, respectively) were obtained.

The titanium contents of the catalysts are expressed as weight % of titania.

Weight % of titania=(molecular weight of titania/atomic weight of titanium)×(weight of titanium/weight of catalyst)×100

A titanium content of each catalyst in the subsequent Examples is also expressed as weight % of titania calculated in the same manner.

(3) Measurement of Physical Properties of Catalyst

From powder X-ray diffraction patterns, the catalysts A to E had a regular two-dimensional hexagonal p6 mm structure. At a titania content of 8.03% by weight or less, no titanium oxide crystal deposition was observed. At a titania content of greater than 8.03% by weight, a weak diffraction pattern attributed to an anatase-type titania nanocrystal was observed. Structural properties of the catalysts measured by nitrogen adsorption are shown in Table 1. The catalysts A to E having a titania content of from 1.07% by weight to 9.18% by weight had a large specific surface area (from 766 m$^2$/g to 890 m$^2$/g), a large pore capacity (from 0.79 cm$^3$/g to 0.96 cm$^3$/g), and controlled mesopores (from 7.1 nm to 7.9 nm).

Figure 3:
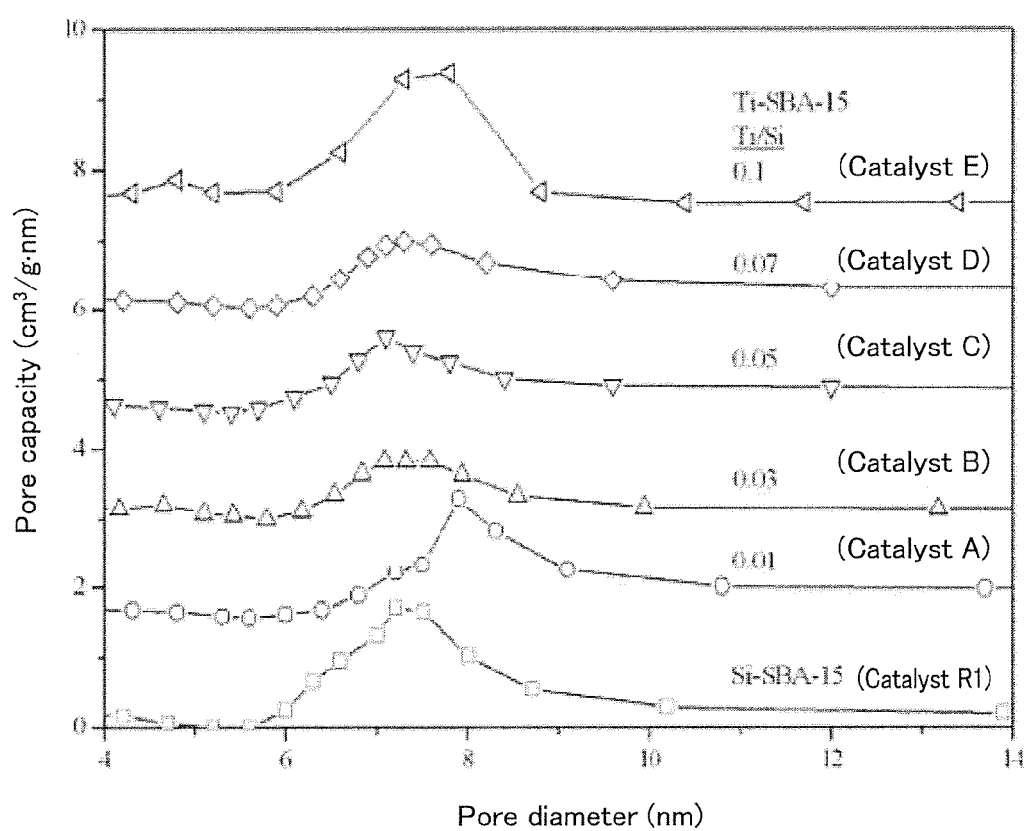
FIG. 3 is a diagram showing pore diameter distributions of Ti-SBA-15 catalysts (A to E, and R1) prepared with different titanium contents, where the distributions are measured by nitrogen adsorption.

Pore diameter distributions of the catalysts A to E and a reference catalyst R1 described later, which were measured by nitrogen adsorption, are shown in FIG. 3.

TABLE 1

| Catalyst | TiO$_2$ (weight %) | Specific surface area (m$^2$/g) | Pore capacity (cm$^3$/g) | Pore diameter (nm) |
|---|---|---|---|---|
| A | 1.07 | 890 | 0.96 | 7.9 |
| B | 2.92 | 840 | 0.91 | 7.6 |
| C | 5.11 | 810 | 0.86 | 7.1 |
| D | 8.03 | 770 | 0.85 | 7.3 |
| E | 9.18 | 766 | 0.79 | 7.3 |

Example 2

Preparation and Physical Property Analysis of Catalysts F and G (1) Preparation of Titanium Precursors Titanium oxychloride precursors were prepared in the same manner as in Example 1 except that the amount of a concentrated hydrochloric acid was changed to 7.65 g (0.078 mol) or 153 g (1.55 mol) (HCl/TTIP molar ratio=1.5 and 30). The obtained titanium oxychloride precursors were transparent yellow solutions, in which no precipitate was observed.

(2) Preparation of Catalysts

Catalysts F and G were prepared in the same manner as in Example 1, except that the titanium oxychloride precursors prepared in Example 2 (1) were used, and the Ti/Si molar ratio in the gel was adjusted to 0.03. Here, the gel composition was P123:silicon:titanium:HCl:NaCl:water=0.013:1:0.03:0.045 or 0.90:1:220.

(3) Measurement of Physical Properties of Catalysts

From powder X-ray diffraction patterns, the catalysts F and G had a regular two-dimensional hexagonal p6 mm structure. Structural properties of the catalysts measured by nitrogen adsorption are shown in Table 2. The catalysts F and G having a titania content of from 0.70% by weight to 4.76% by weight had a large specific surface area (from 792 m$^2$/g to 902 m$^2$/g), a large pore capacity (from 0.80 cm$^3$/g to 1.02 cm$^3$/g), and controlled mesopores (from 7.6 nm to 7.7 nm). The titania contents of the catalysts F and G measured by inductively coupled plasma optical emission spectroscopy (ICP-OES) were 4.76% by weight and 0.70% by weight, respectively. The titania content was lower as the HCl/TTIP molar ratio was higher.

TABLE 2

| Catalyst | TiO$_2$ (weight %) | HCl/TTIP (molar ratio) | Specific surface area (m$^2$/g) | Pore capacity (cm$^3$/g) | Pore diameter (nm) |
| --- | --- | --- | --- | --- | --- |
| F | 4.76 | 1.5 | 792 | 0.80 | 7.7 |
| G | 0.70 | 30 | 902 | 1.02 | 7.6 |

Example 3

Preparation and Physical Property Analysis of Catalysts H and I (1) Preparation of Titanium Precursors Titanium oxychloride precursors were prepared in the same manner as in Example 1.

(2) Preparation of Catalysts

Catalysts H and I were prepared in the same manner as in Example 1, except that in the gel, the Ti/Si molar ratio was changed to 0.03, and the NaCl/TEOS molar ratio was changed to 0 or 6. Here, the gel composition was P123:silicon:titanium:HCl:NaCl:water=0.013:1:0.03:0.075:0 or 6:220.

(3) Measurement of Physical Properties of Catalysts

From powder X-ray diffraction patterns, the catalyst H had a two-dimensional hexagonal p6 mm structure, whereas the catalyst I had a regular pore structure. Structural properties of the catalysts measured by nitrogen adsorption are shown in Table 3. The catalysts H and I had a large specific surface area (from 446 m$^2$/g to 716 m$^2$/g), a large pore capacity (from 0.53 cm$^3$/g to 0.68 cm$^3$/g), and controlled mesopores (7.4 nm). The titania contents of the catalysts H and I measured by inductively coupled plasma optical emission spectroscopy (ICP-OES) were 2.69% by weight and 3.11% by weight, respectively. The titania content was lower as the NaCl/TEOS molar ratio was higher.

TABLE 3

| Catalyst | TiO$_2$ (weight %) | NaCl/TEOS (molar ratio) | Specific surface area (m$^2$/g) | Pore capacity (cm$^3$/g) | Pore diameter (nm) |
| --- | --- | --- | --- | --- | --- |
| H | 3.11 | 0 | 716 | 0.68 | 7.4 |
| I | 2.69 | 6 | 446 | 0.53 | 7.4 |

Example 4

Preparation and Physical Property Analysis of Catalysts J and K (1) Preparation of Titanium Precursors Titanium oxychloride precursors were prepared in the same manner as in Example 1.

(2) Preparation of Catalysts

Catalysts J and K were prepared in the same manner as in Example 1, except that in the gel, the Ti/Si molar ratio was changed to 0.03, the P123/TEOS molar ratio was changed to 0.0087 or 0.022. Here, the gel composition was P123:silicon:titanium:HCl:NaCl:water=0.0087 or 0.022:1:0.03:0.075:1:220.

(3) Measurement of Physical Properties of Catalysts

From powder X-ray diffraction patterns, the catalyst J and K had a regular two-dimensional hexagonal p6 mm structure. Structural properties of the catalysts measured by nitrogen adsorption are shown in Table 4. The catalysts J and K had a large specific surface area (from 775 m$^2$/g to 837 m$^2$/g), a large pore capacity (from 0.87 cm$^3$/g to 0.92 cm$^3$/g), and controlled mesopores (from 7.1 nm to 8.0 nm). The titania contents of the catalysts H and I measured by inductively coupled plasma optical emission spectroscopy (ICP-OES) were 2.98% by weight and 3.50% by weight, respectively. The titania content was lower as the P123/TEOS molar ratio was higher.

TABLE 4

| Catalyst | TiO$_2$ (weight %) | P123/TEOS (molar ratio) | Specific surface area (m$^2$/g) | Pore capacity (cm$^3$/g) | Pore diameter (nm) |
| --- | --- | --- | --- | --- | --- |
| J | 3.50 | 0.0087 | 775 | 0.87 | 7.1 |
| K | 2.98 | 0.022 | 837 | 0.92 | 8.0 |

Example 5

Preparation and Physical Property Analysis of Catalysts L to N (1) Preparation of Titanium Precursors Titanium oxychloride precursors were prepared in the same manner as in Example 1.

(2) Preparation of Catalysts

Catalysts L, M, and N were prepared in the same manner as in Example 1, except that the Ti/Si molar ratio was changed to 0.03, a chloric acid containing 160 g of water was used instead of distilled water, and the concentration of the hydrochloric acid was adjusted to 0.2 M, 0.5 M, and 1.0 M. Here, the gel composition was P123:silicon:titanium:HCl:NaCl:water=0.013:1:0.03:0.47, 0.87, or 2.1:1:220.

(3) Measurement of Physical Properties of Catalysts

From powder X-ray diffraction patterns, the catalyst L, M, and N had a regular two-dimensional hexagonal p6 mm structure. Structural properties of the catalysts measured by nitrogen adsorption are shown in Table 5. The catalysts L, M, and N had a large specific surface area (from 542 m$^2$/g to 840 m$^2$/g), a large pore capacity (from 0.74 cm$^3$/g to 0.91 cm$^3$/g), and controlled mesopores (from 6.5 nm to 7.0 nm). The titania contents of the catalysts L, M, and N measured by inductively coupled plasma optical emission spectroscopy (ICP-OES) were from 0.185% by weight to 3.14% by weight. The titania content was lower as the HCl concentration was higher.

TABLE 5

| Catalyst | TiO$_2$ (weight %) | HCl concentration (M) | Specific surface area (m$^2$/g) | Pore capacity (cm$^3$/g) | Pore diameter (nm) |
| --- | --- | --- | --- | --- | --- |
| L | 3.14 | 0.2 | 840 | 0.91 | 6.8 |
| M | 0.314 | 0.5 | 658 | 0.79 | 7.0 |
| N | 0.185 | 1.0 | 542 | 0.74 | 6.5 |

Example 6

Preparation and Physical Property Analysis of Catalysts O and P (1) Preparation of Titanium Precursors Titanium oxychloride precursors were prepared in the same manner as in Example 1.

(2) Preparation of Catalysts

Trimethyl benzene (TMB) was added after ethyl orthosilicate was added. Catalysts O and P were prepared in the same manner as in Example 1, except that the Ti/Si molar ratio was changed to 0.03, and the molar ratio TMB/P123 was adjusted to 2 or 6. Here, the gel composition was P123:silicon:titanium:HCl:TMB:NaCl:water=0.0087 or 0.022:1:0.03:0.75:1.2 or 3.7:1:220.

(3) Measurement of Physical Properties of Catalysts

From powder X-ray diffraction patterns, the catalyst O and P had an irregular mesostructured cellular form (MCF), respectively. Structural properties of the catalysts measured by nitrogen adsorption are shown in Table 6. The catalysts O and P had a large specific surface area (from 534 $m^2$/g to 562 $m^2$/g), a large pore capacity (from 0.99 $cm^3$/g to 1.13 $cm^3$/g), and controlled mesopores (from 31.1 nm to 37.3 nm).

The titania contents of the catalysts O and P measured by inductively coupled plasma optical emission spectroscopy (ICP-OES) were 2.75% by weight and 3.16% by weight.

TABLE 6

| Catalyst | $TiO_2$ (weight %) | TMB/P123 (mass ratio) | Specific surface area ($m^2$/g) | Pore capacity ($cm^3$/g) | Pore diameter (nm) |
|---|---|---|---|---|---|
| O | 2.75 | 2 | 562 | 0.99 | 5.0-31.1 |
| P | 3.16 | 6 | 534 | 1.13 | 8.7-37.3 |

Figure 4:
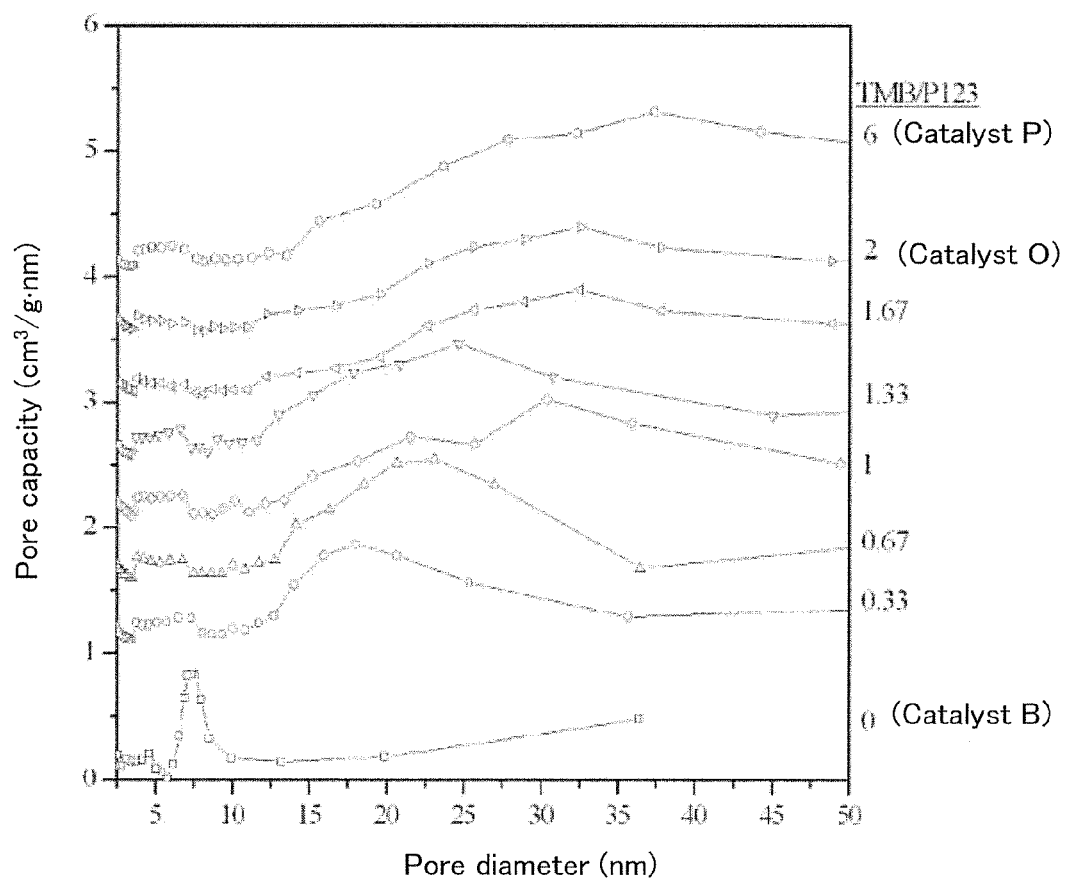
FIG. 4 is a diagram showing pore diameter distributions of Ti-SBA-15 catalysts (B, P, and O) prepared at different TMB/P123 molar ratios, where the distributions are measured by nitrogen adsorption.

Pore diameter distributions, measured by nitrogen adsorption, of the catalyst B obtained in Example 1, and the catalysts O and P obtained in Example 6 where the molar ratio TMB/P123 was changed from 0.33 to 6, are shown in FIG. 4.

The pore diameter increased from 18.2 nm to 37.3 nm as the molar ratio TMB/P123 was increased. It turned out that the pore diameter could be adjusted by changing the molar ratio TMB/P123.

Example 7

Preparation and Physical Property Analysis of Catalysts Q to S (1) Preparation of Titanium Precursors Titanium oxychloride precursors were prepared in the same manner as in Example 1.

(2) Preparation of Catalysts

Catalysts Q, R, and S were prepared in the same manner as in example 1, except that the Ti/Si molar ratio was changed to 0.03, and the burning temperature was changed to 600° C., 700° C., and 800° C.

(3) Measurement of Physical Properties of Catalysts

From powder X-ray diffraction patterns, the catalyst Q, R, and S had a regular two-dimensional hexagonal p6 mm structure. Structural properties of the catalysts measured by nitrogen adsorption are shown in Table 7. The catalysts Q, R, and S had a specific surface area of from 341 $m^2$/g to 618 $m^2$/g, a large pore capacity of from 0.49 $cm^3$/g to 0.70 $cm^3$/g, and mesopores of from 6.5 nm to 6.7 nm. The specific surface area and the pore capacity were lower as the burning temperature was higher.

TABLE 7

| Catalyst | $TiO_2$ (weight %) | Burning temperature (° C.) | Specific surface area ($m^2$/g) | Pore capacity ($cm^3$/g) | Pore diameter (nm) |
|---|---|---|---|---|---|
| Q | 2.92 | 600 | 618 | 0.70 | 6.5 |
| R | 2.92 | 700 | 493 | 0.60 | 6.7 |
| S | 2.92 | 800 | 341 | 0.49 | 6.5 |

Comparative Example 1

As comparative examples, titanium-free SBA-15 and zeolite H-ZSM-5, and titanosilicate TS-1 and titanium-containing mesoporous silica Ti-MCM41, which were catalysts having different structures, were prepared according to the methods described below. Structural properties of the catalysts measured by nitrogen adsorption are shown in Table 8 together with commercially available titania catalysts.

(Preparation of Reference Catalyst R1 (Titanium-Free SBA-15))

Titanium-free SBA-15 was prepared according to a method described in a document (D. Y. Zhao, J. L. Feng, Q. S. Huo; N. Melosh, G. H. Fredrickson, B. F. Chmelka, G. D. Stucky, Science 1998, 279, 548-552). Specifically, in a polypropylene-made bottle, 1 g of a triblock copolymer PLURONIC P123 (manufactured by Sigma-Aldrich Co., LLC., Mn=5800) was added to 40.0 g of a 2 M hydrochloric acid, and dissolved therein at 35° C. for one night. 2.10 g of ethyl orthosilicate (TEOS) was added to the obtained solution. Then, the polypropylene-made bottle was sealed hermetically, stirred at 35° C. for 24 hours, and then subjected to a hydrothermal treatment by being kept stationary at 90° C. for 24 hours. A produced precipitate was filtered, washed with deionized water, and then dried at 50° C. for one night, to thereby obtain a reference catalyst R1.

(Preparation of Reference Catalyst R2 (Zeolite H-ZSM-5))

Commercially available Na-ZSM-5 zeolite (HAZ-820 NAA manufactured by Tosoh Corporation: with a specific surface area of 322 $m^2$/g, $Na_2O$ content of 3.7, and $Al_2O_3$ content of 26) was subjected to ion exchange with 1 M $NH_4NO_3$ three times, and burned in air at 550° C. for 3 hours, to thereby obtain protic H-ZSM-5 (reference catalyst R2).

(Preparation of Reference Catalyst R7 (Titanium-Containing Mesoporous Silica Ti-MCM-41))

A titanium-containing mesoporous silica Ti-MCM-41 was prepared according to a method described in a document (D. Srinivas, R. Srivastava, P. Ratnasamy, Catal. Today 2004, 96, 127-133). Specifically, a reference catalyst R7 was prepared according to the method described in the document identified above, using 10.9 g of 25% by weight tetramethyl ammonium hydroxide (TMAOH) and 72 g of deionized water as raw material.

(Preparation of Reference Catalyst (Titanosilicate TS-1))

Commercially available titanosilicate TS-1 (ARC-TS-1CL, with a $SiO_2/TiO_2$ molar ratio=35) was treated with 1 M $NH_4NO_3$ three times, and burned in air at 550° C. for 3 hours, to thereby obtain a titanosilicate TS-1 catalyst (reference catalyst R6).

(Crystal Size of Reference Catalysts (Commercially Available Titania Catalysts))

The commercially available titania catalysts R3 to R5 used as the reference catalysts had a crystal size of 84.7 nm (reference catalyst R3), 25.5 nm (reference catalyst R4), and 15 nm (reference catalyst R5), respectively.

TABLE 8

| Reference catalyst | Commercially available catalyst name | $TiO_2$ or $Al_2O_3$ (weight %) | Specific surface area ($m^2/g$) | Pore capacity ($cm^3/g$) | Pore diameter (nm) |
|---|---|---|---|---|---|
| R1 | SBA-15 | 0 | 914 | 1.10 | 7.5 |
| R2 | H-ZSM-5 | 3.70 | 343 | 0.23 | 0.6 |
| R3 | JRC-TIO-2 | 100 | 11 | 0.10 | — |
| R4 | $TiO_2$ | 100 | 128 | 0.32 | 10.0 |
| R5 | 35E-$TiO_2$ | 100 | 164 | 0.38 | 10.1 |
| R6 | TS1-CL | 2.39 | 406 | 0.24 | 0.6 |
| R7 | Ti-MCM-41 | 3.00 | 1,200 | 0.89 | 2.8 |

(Composition and Properties of Raw Material Oils)

A composition analysis of the raw material oils was conducted according to an IUPAC method ("2.301. Preparation of the Fatty Acid Methyl Esters"), and an average molecular weight thereof was calculated. In the composition analysis of the oils, 0.5 g of an oil was mixed with 7 mL of 0.5 M sodium hydroxide/methanol solution, and heated and stirred at 80° C. for 10 minutes. 8 mL of boron trifluoride/methanol solution was added thereto, and they were heated and stirred at the same temperature for 5 minutes. 7 mL of heptane was added to the resulting solution, and they were stirred for 1 minute. An appropriate amount of a saturated saline was further added thereto, and a resulting separated top layer was dried out with an anhydrous sodium sulfate, to thereby obtain a fatty acid methyl ester solution. This solution was analyzed with a gas chromatograph equipped with a HP-88 capillary column (with an inner diameter of 0.25 mm, a length of 60 m, and a film thickness of 0.25 μm), to obtain a fatty acid composition of the oil. The acid value of the oil was analyzed and calculated according to JIS K 2501. The properties of the oils are shown in Table 9.

(Method for Preparing Biodiesel Fuels)

Synthesis of biodiesel fuels through transesterification between an oil and methanol with the catalysts of the present invention and the reference catalysts was performed according to the following procedure. Specifically, a glass-made test tube into which 5 g of an oil, 5 g of methanol, and 0.75 g of a catalyst dried in advance at 110° C. for 2 hours were put was inserted into a stainless steel-made high-pressure autoclave (with an inner diameter of 1.8 mm, and a length of 30 cm), and after nitrogen purging, the test tube was heated and stirred at 200° C. for 3 hours. Then, the test tube was cooled to room temperature, the catalyst was filtered out, excess methanol was removed, and then the biodiesel fuel at the top layer was subjected to an analysis.

(Quantification of Fatty Acid Methyl Ester and Free Fatty Acid Contents of Biodiesel Fuels)

Quantification of fatty acid methyl ester (FAME) and free fatty acid (FFA) contents of the biodiesel fuels was performed according to the following procedure. Specifically, 1004 of N-methyl-N-trimethyl silyl trifluoroacetamide (MSTFA) was added to 0.1 g of a biodiesel fuel, and they were reacted for at least 15 minutes, to silylate glycerin, monoglyceride, diglyceride, and a free fatty acid. To which, 2 mL of a methyl heptadecanoate solution (a 10 mg/mL heptane solution) was added as an internal standard, and the resultant was diluted with 5 mL of heptane, and then analyzed with a gas chromatograph equipped with a HP-1 capillary column (with an internal diameter of 0.25 mm, a length of 60 m, and a film thickness of 0.25 μm), to calculate

TABLE 9

| | Jatropha oil | Waste food oil | Canola oil | Soy oil | PFAD | Crude palm oil |
|---|---|---|---|---|---|---|
| Property | | | | | | |
| Average molecular weight (g/mol) | 892 | 879 | 882 | 875 | 830 | 849 |
| Acid value (mg KOH/g) | 17.76 | 1.47 | 0.12 | 0.06 | 189.94 | 13.51 |
| Free fatty acid content (wt %) | 9.03 | 0.74 | 0.06 | 0.03 | 89.5 | 6.52 |
| Fatty acid composition (wt %) | | | | | | |
| Lauric acid (12:0) | 0 | 0.03 | 0.01 | 0 | 0.17 | 0.31 |
| Myristic acid (14:0) | 0.06 | 0.11 | 0.05 | 0.07 | 1.50 | 1.10 |
| Palmitic acid (16:0) | 14.40 | 7.40 | 4.20 | 10.00 | 65.00 | 44.00 |
| Palmitoleic acid (16:1) | 0.89 | 0.33 | 0.28 | 0.13 | 0.19 | 0.21 |
| Margaric acid (17:0) | 0.10 | 0.08 | 0.055 | 0.10 | 0.22 | 0.11 |
| Stearic acid (18:0) | 6.84 | 2.90 | 1.9 | 4.10 | 5.1 | 4.30 |
| Oleic acid (18:1) | 41.80 | 49.00 | 61.00 | 24.00 | 20.00 | 39.00 |
| Linoleic acid (18:2) | 34.75 | 30.00 | 20.00 | 51.00 | 2.20 | 9.60 |
| Linolenic acid (18:3) | 0.19 | 7.60 | 9.10 | 7.80 | 0.1 | 0.30 |
| Arachidic acid (20:0) | 0.21 | 0.58 | 0.50 | 0.56 | 0.34 | 0.37 |
| Gadoleic acid (20:1) | 0.08 | 0.93 | 1.32 | 0.33 | 0.13 | 0.16 |
| Behenic acid (22:0) | 0.04 | 0.34 | 0.35 | 0.38 | 0.16 | 0.07 |
| Lignoceric acid (24:0) | 0.06 | 0.16 | 0.16 | 0.13 | 0.06 | 0.11 | the fatty acid methyl ester (FAME) and free fatty acid (FFA) contents were according to the following formula (1).

$$C_x = \frac{\sum A_{total}}{A_{mp}} \times \frac{C_{mp} \times V_{mp}}{m} \times 100\% \quad (1)$$

where Cx: a FAME (or FFA) content, $\Sigma A_{total}$: a total of peak areas of fatty acid methyl esters of which carbon numbers are from 14 to 24 (or a total of peak areas of free fatty acids of which carbon numbers are from 16 to 20), $A_{mp}$: a peak area of methyl heptadecanoate (internal standard), $C_{mp}$: the concentration (mg/mL) of the methyl heptadecanoate solution, $V_{mp}$: the amount (mL) of the methyl heptadecanoate solution, and m: the weight of a sample.

(Quantification of Glycerin and Glyceride Contents of Biodiesel Fuels)

Quantification of glycerin and glyceride contents of the biodiesel fuels was performed according to an European standard EN14105:2003. Specifically, 80 μl of 1,2,4-butanetriol (a 1 mg/mL pyridine solution) as an internal standard for glycerin quantification, and 100 μL of tricaprin (a 8 mg/mL pyridine solution) as an internal standard for glyceride quantification were added to 0.1 g of a biodiesel fuel, and 100 μL of N-methyl-N-trimethyl silyl trifluoroacetamide (MSTFF) was further added thereto. They were reacted for at least 15 minutes, to silylate glycerin, monoglyceride, and diglyceride. The resultant was diluted with 7 mL of heptane, and analyzed with a gas chromatograph equipped with a DB-5HT capillary column (with an internal diameter of 0.25 mm, a length of 30 m, and a film thickness of 0.1 μm), to calculate glycerin and glyceride contents, and at the same time, calculate a total glycerin amount according to the following formula (2)

$$Gr = G + 0.255MG + 0.146DG + 0.103TG \quad \text{Formula (2)}$$

where in the formula, Gr: a total glycerin amount in the sample, G: a free glycerin amount in the sample, MG: a monoglyceride amount in the sample, DG: a diglyceride amount in the sample, and TG: a triglyceride amount in the sample.

In the quality standards for a biodiesel fuel to be mixed with a light oil (Japanese JIS K2390:2008, European EN14214:2003, U.S. D6751:2012, and Eastern Asia Summit-encouraged standard EEBS:2008), it is stipulated that a fatty acid methyl ester content should be 96.5% by mass or greater, and contents of total glycerin, monoglyceride, diglyceride, triglyceride, and free glycerin should be 0.25% by mass or less, 0.2% by mass or less, 0.2% by mass or less, 0.8% by mass or less, and 0.02% by mass or less, respectively.

Example 8

Reactions Using Ti-SBA-15 Catalysts a to E with Different Titanium Contents of Example 1

Table 10 shows the results of transesterification of a jatropha oil with the catalysts A to E of the present invention. Reactions were induced according to the method described in (Method for Preparing Biodiesel Fuels) at a methanol/oil molar ratio of 27, and at an oil/catalyst ratio by weight of 15. When reactions were induced with the catalysts A to E, i.e., the titanium-containing SBA-15 mesoporous silica catalysts with titania contents of from 1.07% by mass to 9.18% by mass, fatty acid methyl ester yields were from 74.6% by mass to 90.9% by mass, and total glycerin amounts were from 1.6% by mass and 4.3% by mass. With the catalysts A to D having titania contents of from 1.07% by mass to 8.03% by mass, fatty acid methyl ester yields were from 83.9% by mass to 90.9% by mass, and total glycerin amounts were from 1.6% by mass to 2.8% by mass. Further, with only the catalysts B and C having titania contents of 2.92% by mass and 5.11% by mass, fatty acid methyl ester yields were 89.5% by mass or greater, and total glycerin amounts were 1.7% by mass or less. As compared with the catalyst E that showed a clear anatase-type diffraction pattern, the catalysts A to D that did not show a clear anatase-type diffraction pattern in powder X-ray diffraction provided relatively high fatty acid methyl ester yields, with low total glycerin amounts.

Comparative Example 2

Reactions Using Reference Catalysts R1 to R7 of Comparative Example 1

Table 10 shows the results of transesterification of a jatropha oil with the reference catalysts R1 to R7. Reactions were induced under the same conditions as in Example 8.

With the reference catalysts R1 and R2, fatty acid methyl ester yields were low and 21.8% by mass and 23.9% by mass, respectively, and total glycerin amounts were high and 7.0% by mass and 9.4% by mass, respectively. That is, the fact that the fatty acid methyl ester yields were low with SBA-15 that had the same structure as the present invention but was titanium-free, and with an aluminosilicate H-ZSM-5 indicated that the titanium species of the catalysts of the present invention were active species in the synthesis of a biodiesel fuel.

With the reference catalysts R3 to R5, which were pure titania, fatty acid methyl ester yields were low, and 33.9% by mass, 39.8% by mass, and 54.9% by mass, respectively, but the yields were higher as the crystal size of the catalysts was smaller. Total glycerin amounts were high, and 7.8% by mass, 7.9% by mass, and 5.9% by mass.

With the reference catalysts R6 and R7 containing titania and silica, fatty acid methyl ester yields were 68.8% by mass and 83.4 by mass, respectively, which were lower than with the catalysts of the present invention. On the other hand, total glycerin amounts were 4.5% by mass and 2.5% by mass. R7, which had a larger pore diameter than that of R6, resulted in a higher fatty acid methyl ester yield than that of R6, which indicated that the yield was largely dependent on the pore diameter.

Figure 5A:
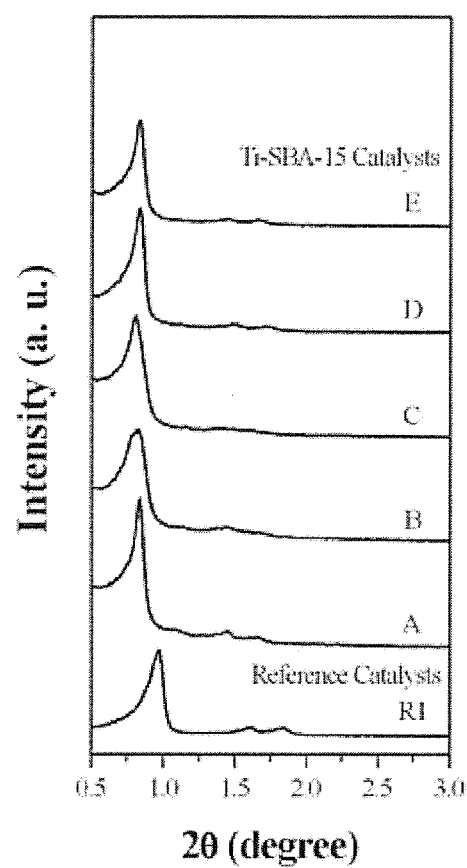
FIG. 5A is a diagram showing powder X-ray diffraction patterns of catalysts A to E and a reference catalyst R1 at a small angle.
Figure 5B:
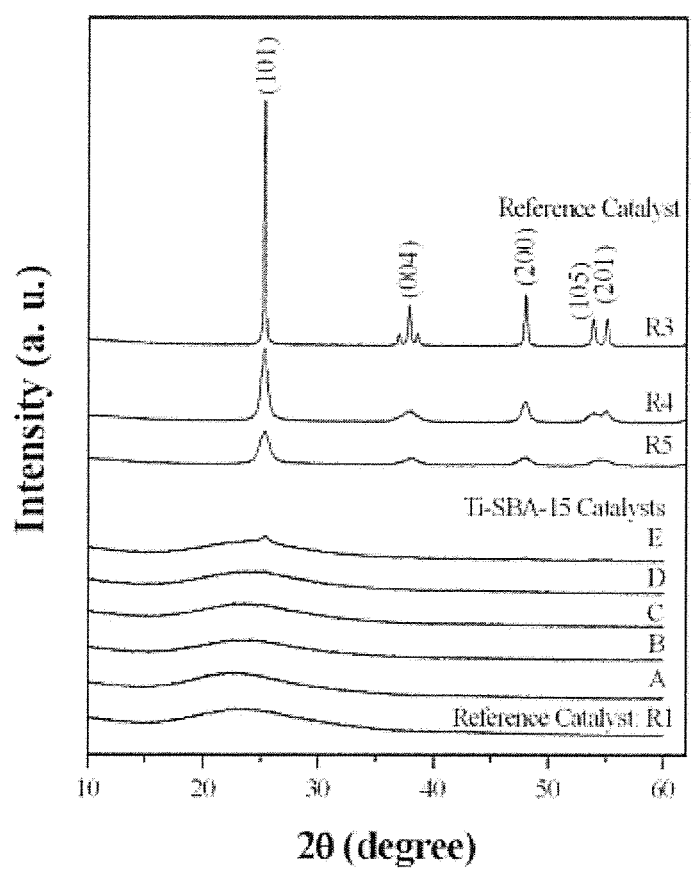
FIG. 5B is a diagram showing powder X-ray diffraction patterns of catalysts A to E and reference catalysts R1 and R3 to R5 at a wide angle.

FIG. 5A and FIG. 5B show powder X-ray diffraction patterns of the catalysts A to E and Catalysts R1 and R3 to R5 obtained in the above Example and Comparative Example at a small angle and a wide angle. Shorter half-value widths of the peaks on the graph of FIG. 5B indicate higher crystallinity of the catalysts. R3 to R5, which resulted in low transesterification yields, had high crystallinity degrees. In a comparison within the catalysts A to E, crystallinity was observed in the catalyst E that resulted in the lowest transesterification yield. From these results, it turned out that catalysts having an amorphous structure had a higher transesterification efficiency than that of catalysts having a crystalline structure.

TABLE 10

| Catalyst | TiO$_2$ or Al$_2$O$_3$ content (weight %) | Carrier | FAME (mass %) | Total glycerin (mass %) | Triglyceride (mass %) | Diglyceride (mass %) | Monoglyceride (mass %) | Free glycerin (mass %) |
|---|---|---|---|---|---|---|---|---|
| No catalyst | — | — | 23.2 | 9.0 | 35.0 | 28.0 | 3.7 | 0.34 |
| A Ti-SBA-15 | 1.07 | SBA-15 | 83.9 | 2.8 | 3.2 | 4.2 | 6.6 | 0.15 |
| B | 2.92 | SBA-15 | 90.9 | 1.6 | 1.5 | 1.5 | 4.3 | 0.17 |
| C | 5.11 | SBA-15 | 89.5 | 1.7 | 1.8 | 2.2 | 4.2 | 0.17 |
| D | 8.03 | SBA-15 | 85.8 | 2.3 | 3.3 | 3.7 | 5.0 | 0.17 |
| E | 9.18 | SBA-15 | 74.6 | 4.3 | 2.6 | 7.1 | 11.0 | 0.16 |
| R1 Si-SBA-15 | 0 | SBA-15 | 23.9 | 9.4 | 33.0 | 33.0 | 4.1 | 0.12 |
| R2 H-ZSM-5 | 3.70 | ZSM-5 | 21.8 | 7.0 | 27.0 | 22.0 | 3.7 | 0.02 |
| R3 JRC-TIO-2 | 100 | No | 33.9 | 7.8 | 38.0 | 20.0 | 3.2 | 0.18 |
| R4 TiO$_2$-p | 100 | No | 39.8 | 7.9 | 32.0 | 18.0 | 4.4 | 0.81 |
| R5 35E-TiO$_2$ | 100 | No | 54.9 | 5.9 | 20.0 | 16.0 | 5.0 | 0.23 |
| R6 TS1-CL | 2.39 | ZSM-5 | 68.8 | 4.5 | 15.0 | 8.7 | 6.1 | 0.12 |
| R7 Ti-MCM-41 | 3.00 | MCM-41 | 83.4 | 2.5 | 6.5 | 5.3 | 3.4 | 0.18 |

Example 9

Effect of Methanol/Oil Ratio

Biodiesel fuels were synthesized in the same manner as in Example 8, except that the catalyst B was used, and a methanol/oil molar ratio was changed from 27 to 216. As the methanol/oil ratio was increased, the fatty acid methyl ester yield increased, and at a methanol/oil ratio of 108, a high-quality biodiesel fuel was obtained at a fatty acid methyl ester yield of 98.1% by mass and at a total glycerin amount of 0.16% by mass. Residual triglyceride, diglyceride, monoglyceride, and free glycerin amounts were 0.03% by mass, 0.04% by mass, 0.55% by mass, and 0.01% by mass, which satisfied the biodiesel fuel standards. A titanium concentration in the biodiesel fuel was measured by inductively coupled plasma optical emission spectroscopy (ICP-OES) according to the same method as European standard prEN 14538. As a result, titanium was detected in none of the cases, which indicated that there was no titanium leaching.

TABLE 11

| Catalyst | MeOH/Oil molar ratio | FAME (mass %) | Total glycerin (mass %) | Triglyceride (mass %) | Diglyceride (mass %) | Monoglyceride (mass %) | Free glycerin (mass %) | Ti (ppm) |
|---|---|---|---|---|---|---|---|---|
| Catalyst B | 27 | 90.9 | 1.64 | 1.50 | 1.50 | 4.30 | 0.17 | 0 |
| | 54 | 96.0 | 0.65 | 0.24 | 0.31 | 2.00 | 0.07 | 0 |
| | 81 | 97.7 | 0.25 | 0.05 | 0.06 | 0.89 | 0.01 | 0 |
| | 108 | 98.1 | 0.16 | 0.03 | 0.04 | 0.55 | 0.01 | 0 |
| | 135 | 98.4 | 0.16 | 0.03 | 0.04 | 0.57 | 0.01 | — |
| | 162 | 98.9 | 0.11 | 0.02 | 0.04 | 0.34 | 0.01 | — |
| | 189 | 98.8 | 0.09 | 0.01 | 0.02 | 0.30 | 0.01 | — |
| | 216 | 98.7 | 0.10 | 0.01 | 0.01 | 0.34 | 0.01 | — |
| Reference Catalyst R6 | 27 | 68.8 | 4.50 | 15.00 | 8.70 | 6.10 | 0.12 | 0 |
| Jatropha oil | — | — | — | — | — | — | — | 0 |

Example 10

Effects of Nitrogen Pressurization and Reaction Time

Biodiesel fuels were synthesized in the same manner as in Example 8, except that the catalyst B was used, a methanol/oil molar ratio was set to 108, a reaction time was set to 0.5 hours or 3 hours, and an autoclave was previously pressurized with nitrogen at 0 to 40 bar. The fatty acid methyl ester yield was higher as the reaction time was longer, and biodiesel fuels obtained from the 3-hour reaction satisfied the fuel standards. Meanwhile, substantially no effect of nitrogen pressurization was observed.

TABLE 12

| Nitrogen pressurization (bar) | Reaction time (h) | FAME (mass %) | Total glycerin (mass %) | Triglyceride (mass %) | Diglyceride (mass %) | Monoglyceride (mass %) | Free glycerin (mass %) |
|---|---|---|---|---|---|---|---|
| 0 | 0.5 | 86.8 | 2.8 | 0.64 | 3.2 | 8.7 | 0.033 |
| 10 | 0.5 | 85.3 | 3.0 | 1.0 | 3.9 | 8.7 | 0.10 |
| 20 | 0.5 | 88.1 | 2.4 | 0.7 | 2.9 | 7.2 | 0.10 |

TABLE 12-continued

| Nitrogen pressurization (bar) | Reaction time (h) | FAME (mass %) | Total glycerin (mass %) | Triglyceride (mass %) | Diglyceride (mass %) | Monoglyceride (mass %) | Free glycerin (mass %) |
| --- | --- | --- | --- | --- | --- | --- | --- |
| 30 | 0.5 | 86.6 | 2.8 | 0.78 | 3.42 | 8.1 | 0.11 |
| 40 | 0.5 | 86.4 | 2.8 | 0.8 | 3.5 | 8.2 | 0.09 |
| 0 | 3 | 98.1 | 0.16 | 0.032 | 0.044 | 0.55 | 0.010 |
| 10 | 3 | 98.4 | 0.19 | 0.063 | 0.029 | 0.66 | 0.010 |
| 30 | 3 | 98.5 | 0.20 | 0.029 | 0.027 | 0.72 | 0.010 |

Example 11

Effect of Water Addition (Examination of Water Resistance)

Biodiesel fuels were synthesized in the same manner as in Example 8, except that the catalyst B was used, a methanol/oil molar ratio was set to 108, a reaction time was set to 3 hours or 6 hours, an amount of water addition was set to 0% by weight to 10% by weight. In the cases where the reaction time was 3 hours, the obtained biodiesel fuels satisfied the fuel standards, provided that the amount of water addition was 2% by weight or less. On the other hand, in the cases where the amount of water addition was from 3% by weight to 5% by weight, it was possible to obtain biodiesel fuels satisfying the fuel standards by setting the reaction time to 6 hours. From these results, it can be seen that the catalyst of the present invention had a high water resistance. The reason for this is considered to be a lower acid level of the catalyst of the present invention than that of Ti-MCM-41, which made contribution of the water presence to the catalyst activity dropping low.

Example 12

Effect of Free Fatty Acid Addition (Examination of Free Fatty Acid Resistance)

Biodiesel fuels were synthesized in the same manner as in Example 8, except that the catalyst B was used, a methanol/oil ratio was set to 108, a reaction time was set to 3 hours or 6 hours, and a myristic acid was added as a free fatty acid in an amount of from 0% by weight to 50% by weight. In the cases where the amount of myristic acid addition was 30% by weight or less, the obtained biodiesel fuels satisfied the fuel standards, provided that the reaction time was 3 hours, and the amount of water addition was 2% by weight or less. On the other hand, in the cases where the amount of myristic acid addition was 40% by mass, it was possible to obtain a biodiesel fuel satisfying the fuel standards by performing water washing, although a glycerin amount exceeded the fuel standard value. From these results, it can be seen that the catalyst of the present invention had a high free fatty acid resistance.

TABLE 13

| Water/oil (mass %) | Reaction time (h) | FAME (mass %) | Total glycerin (mass %) | Triglyceride (mass %) | Diglyceride (mass %) | Monoglyceride (mass %) | Free glycerin (mass %) |
| --- | --- | --- | --- | --- | --- | --- | --- |
| 0 | 3 | 97.8 | 0.22 | 0.032 | 0.044 | 0.77 | 0.010 |
| 1 | 3 | 97.9 | 0.18 | 0.030 | 0.030 | 0.64 | 0.005 |
| 2 | 3 | 97.7 | 0.20 | 0.040 | 0.070 | 0.71 | 0.006 |
| 3 | 6 | 97.7 | 0.17 | 0.026 | 0.052 | 0.59 | 0.006 |
| 4 | 6 | 97.8 | 0.18 | 0.037 | 0.065 | 0.61 | 0.008 |
| 5 | 6 | 97.7 | 0.20 | 0.026 | 0.066 | 0.69 | 0.007 |
| 6 | 6 | 97.0 | 0.28 | 0.042 | 0.10 | 1.0 | 0.011 |
| 10 | 6 | 93.8 | 0.77 | 0.13 | 0.60 | 2.5 | 0.029 |

TABLE 14

| Free fatty acid | Free fatty acid/oil (weight %) | Free fatty acid conversion rate (%) | FAME (mass %) | Total glycerin (mass %) | Triglyceride (mass %) | Diglyceride (mass %) | Monoglyceride (mass %) | Free glycerin (mass %) |
| --- | --- | --- | --- | --- | --- | --- | --- | --- |
| Myristic acid | 0 | — | 97.8 | 0.22 | 0.032 | 0.064 | 0.77 | 0.010 |
| | 30 | 99.2 | 98.0 | 0.17 | 0.053 | 0.055 | 0.53 | 0.020 |
| | 40 | 98.7 | 97.4 | 0.22 | 0.064 | 0.084 | 0.66 | 0.030 |
| | 50 | 98.4 | 97.1 | 0.25 | 0.050 | 0.11 | 0.77 | 0.030 |

Example 13

Effect of Repeated Use

With a repeated use of a catalyst, biodiesel fuels were synthesized in the same manner as in Example 8, except that the catalyst B was used, a methanol/oil molar ratio was set to 108, and an oil/catalyst ratio by weight was set to 15. A used catalyst to be used repeatedly was such a catalyst that, after a previous reaction, was to be filtered, washed with an appropriate amount of acetone, dried at 50° C. for one night, and burned in air at 500° C. for 3 hours. The used catalyst was reduced in the specific surface area and the pore capacity from those of the unused catalyst, but was not substantially changed in the pore diameter, and a biodiesel fuel satisfying the fuel standards was obtained.

Further, experiments under the same conditions were conducted using Ti-MCM-41 prepared in Comparative Example 1. A reaction using an unused Ti-MCM-41 resulted in 0.26% by mass of total glycerin and 0.87% by mass of monoglyceride, which did not satisfy the fuel standards. In the case where a reclaimed Ti-MCM-41 was used, total glycerin increased to 0.29% by mass, and monoglyceride increased to 1.0% by mass, respectively.

From these results, the catalyst of the present invention could be used repeatedly, and a high biodiesel fuel synthesizing activity could be maintained through a simple reclaiming process.

TABLE 15

| Number of repetition | Specific surface area ($m^2/g$) | Pore capacity ($cm^3/g$) | Pore diameter (nm) | FAME (mass %) | Total glycerin (mass %) | Triglyceride (mass %) | Diglyceride (mass %) | Monoglyceride (mass %) | Free glycerin (mass %) |
|---|---|---|---|---|---|---|---|---|---|
| Unused catalyst C500-3Ti-SBA-15 (B) | 840 | 0.91 | 7.6 | 98.4 | 0.19 | 0.040 | 0.079 | 0.66 | 0.010 |
| 1 | 528 | 0.72 | 7.3 | 98.5 | 0.18 | 0.032 | 0.041 | 0.63 | 0.0070 |
| 2 | 538 | 0.72 | 7.4 | 98.5 | 0.20 | 0.055 | 0.052 | 0.71 | 0.0061 |
| Unused catalyst MCM-41 (R7) | 1,200 | 0.89 | 2.8 | 98.1 | 0.26 | 0.05 | 0.17 | 0.87 | 0.01 |
| 1 | 826 | 0.52 | 2.7 | 98.0 | 0.29 | 0.06 | 0.11 | 1.00 | 0.02 |

Example 14

Effect of Titania Precursor Preparation

Biodiesel fuels were synthesized in the same manner as in Example 8, except that the catalysts B, F, and G prepared by varying the HCl/TTIP molar ratio were used, a methanol/oil molar ratio was set to 108, and an oil/catalyst ratio by weight was set to 15. With the HCl/TTIP molar ratio varied, catalysts having different titania contents were obtained, and in all of the cases, biodiesel fuels satisfying the fuel standards were obtained. From the result, it can be seen that the catalyst of the present invention provided a high biodiesel fuel synthesizing activity, even when the HCl/TTIP molar ratio in the preparation of a titanium precursor was varied in the range of from 1.5 to 30.

TABLE 16

| Catalyst | HCl/TTIP (molar ratio) | $TiO_2$ (weight %) | FAME (mass %) | Total glycerin (mass %) | Triglyceride (mass %) | Diglyceride (mass %) | Monoglyceride (mass %) | Free glycerin (mass %) |
|---|---|---|---|---|---|---|---|---|
| B | 3 | 2.92 | 98.4 | 0.19 | 0.040 | 0.079 | 0.66 | 0.010 |
| F | 1.5 | 4.76 | 97.9 | 0.23 | 0.056 | 0.100 | 0.77 | 0.009 |
| G | 30 | 0.70 | 98.3 | 0.22 | 0.034 | 0.055 | 0.78 | 0.011 |

Example 15

Effect of Amount of Sodium Chloride Addition in Preparation

Biodiesel fuels were synthesized in the same manner as in Example 8, except that the catalysts B, H, and I prepared by varying the NaCl/TEOS molar ratio were used, a methanol/oil molar ratio was set to 108, and an oil/catalyst ratio by weight was set to 15. With the NaCl/TEOS molar ratio varied, catalysts having different structures were obtained, and in all of the cases, biodiesel fuels satisfying the fuel standards were obtained. From the result, it can be seen that the catalyst of the present invention provided a high biodiesel fuel synthesizing activity, even when the NaCl/TEOS molar ratio in the preparation of the catalyst was varied in the range of from 0 to 6.

TABLE 17

| Catalyst | NaCl/TEOS (molar ratio) | $TiO_2$ (weight %) | FAME (mass %) | Total glycerin (mass %) | Triglyceride (mass %) | Diglyceride (mass %) | Monoglyceride (mass %) | Free glycerin (mass %) |
|---|---|---|---|---|---|---|---|---|
| B | 2 | 2.92 | 98.4 | 0.19 | 0.040 | 0.079 | 0.66 | 0.010 |
| H | 0 | 3.11 | 98.2 | 0.23 | 0.070 | 0.084 | 0.75 | 0.016 |
| I | 6 | 2.69 | 98.3 | 0.23 | 0.060 | 0.063 | 0.79 | 0.015 |

Example 16

Effect of Amount of P123 Addition in Preparation

Biodiesel fuels were synthesized in the same manner as in Example 8, except that the catalysts B, J, and K prepared by varying the P123/TEOS molar ratio were used, a methanol/oil molar ratio was set to 108, and an oil/catalyst ratio by weight was set to 15. All of the catalysts having the varied P123/TEOS molar ratios provided biodiesel fuels satisfying the fuel standards. From the result, it can be seen that the catalyst of the present invention provided a high biodiesel fuel synthesizing activity, even when the P123/TEOS molar ratio in the preparation of the catalyst was varied in the range of from 0.0087 to 0.022.

TABLE 18

| Catalyst | P123/TEOS (molar ratio) | $TiO_2$ (weight %) | FAME (mass %) | Total glycerin (mass %) | Triglyceride (mass %) | Diglyceride (mass %) | Monoglyceride (mass %) | Free glycerin (mass %) |
|---|---|---|---|---|---|---|---|---|
| B | 0.013 | 2.92 | 98.4 | 0.19 | 0.04 | 0.079 | 0.66 | 0.010 |
| J | 0.0087 | 3.50 | 98.2 | 0.22 | 0.13 | 0.11 | 0.70 | 0.014 |
| K | 0.022 | 2.98 | 98.2 | 0.24 | 0.17 | 0.12 | 0.72 | 0.016 |

Example 17

Effect of Amount of Chloric Acid Addition in Catalyst Preparation

Biodiesel fuels were synthesized in the same manner as in Example 8, except that the catalyst B, and the catalysts L, M, and N prepared by adding a hydrochloric acid during the catalyst preparation were used, a methanol/oil molar ratio was set to 108, and an oil/catalyst ratio by weight was set to 15. All of the catalysts that fell under the condition that it was prepared with distilled water only or that it had a hydrochloric acid concentration of 0.1 M provided biodiesel fuels satisfying the fuel standards. A hydrochloric acid concentration of higher than 0.1 M lowered the titanium content, which made it impossible to obtain a sufficient catalyst activity. From these results, it can be seen that the catalyst of the present invention could contain a sufficient amount of titanium and provide a high biodiesel fuel synthesizing activity, when prepared to a weak acidic level with a hydrochloric acid concentration set to 0.1 M or lower in the catalyst preparation.

TABLE 19

| Catalyst | Hydrochloric acid (molarity) | TiO$_2$ (weight %) | FAME (mass %) | Total glycerin (mass %) | Triglyceride (mass %) | Diglyceride (mass %) | Monoglyceride (mass %) | Free glycerin (mass %) |
|---|---|---|---|---|---|---|---|---|
| B | 0 | 2.92 | 98.4 | 0.19 | 0.04 | 0.079 | 0.66 | 0.010 |
| L | 0.1 | 3.14 | 96.9 | 0.53 | 0.13 | 0.16 | 1.8 | 0.037 |
| M | 0.5 | 0.314 | 66.8 | 5.19 | 12.0 | 14.0 | 5.7 | 0.46 |
| N | 1.0 | 0.185 | 55.5 | 7.33 | 9.3 | 19.0 | 13.0 | 0.28 |

Example 18

Effect of Pore Control by Trimethyl Benzene Addition

Biodiesel fuels were synthesized in the same manner as in Example 8, except that the catalyst B, and the catalyst O and P prepared by adding trimethyl benzene during the catalyst preparation were used, a methanol/oil molar ratio was set to 108, and an oil/catalyst ratio by weight was set to 15. All of the catalysts prepared by adding trimethyl benzene had a three-dimensional irregular mesostructured cellular form, but provided biodiesel fuels satisfying the fuel standards because a high dispersibility of titanium was maintained in these catalysts.

TABLE 20

| Catalyst | TiO$_2$ (weight %) | TMB/P123 (ratio by weight) | Pore structure | FAME (mass %) | Total glycerin (mass %) | Triglyceride (mass %) | Diglyceride (mass %) | Monoglyceride (mass %) | Free glycerin (mass %) |
|---|---|---|---|---|---|---|---|---|---|
| B | 2.92 | 0 | 2D hexagonal p6mm | 98.4 | 0.19 | 0.040 | 0.079 | 0.66 | 0.010 |
| O | 2.75 | 2 | 3D MCF | 98.4 | 0.21 | 0.045 | 0.054 | 0.74 | 0.011 |
| P | 3.16 | 6 | 3D MCF | 98.3 | 0.22 | 0.059 | 0.049 | 0.75 | 0.015 |

Example 19

Effect of Burning Temperature

Biodiesel fuels were synthesized in the same manner as in Example 8, except that the catalyst B, and a catalyst S that was prepared under the same conditions as the catalyst B but burned at 800° C. were used, a methanol/oil molar ratio was set to 108, an oil/catalyst ratio by weight was set to 15, and a reaction time was set to 0.5 hours or 3 hours. A reaction time of 3 hours resulted in biodiesel fuels satisfying the fuel standards. It did not make a major difference in the biodiesel fuel reaction activity whether the burning temperature was 500° C. or 800° C.

Example 20

Effect of Oil Type

Biodiesel fuels were synthesized in the same manner as in Example 8, except that the catalyst B was used, a methanol/oil molar ratio was set to 108, an oil/catalyst ratio by weight was set to 15 or 30, a reaction time was set to 3 hours or 5 hours, and a jatropha oil, a palm oil, a waste food oil, a palm fatty acid distillation product (PFAD: a by-product of palm oil refinement), a soy oil, and a canola oil were used as oils. In all of the cases, biodiesel fuels satisfying the fuel standards were obtained.

TABLE 21

| Catalyst | Titania content (weight %) | Burning temperature (° C.) | Reaction time (h) | FAME (mass %) | Total glycerin (mass %) | Triglyceride (mass %) | Diglyceride (mass %) | Monoglyceride (mass %) | Free glycerin (mass %) |
|---|---|---|---|---|---|---|---|---|---|
| B | 2.92 | 500 | 0.5 | 89.9 | 1.6 | 1.5 | 1.5 | 4.3 | 0.17 |
|   |      |     | 3   | 98.4 | 0.19 | 0.040 | 0.079 | 0.66 | 0.010 |
| S | 2.92 | 800 | 0.5 | 92.8 | 1.4 | 0.50 | 0.57 | 4.5 | 0.13 |
|   |      |     | 3   | 98.2 | 0.23 | 0.059 | 0.058 | 0.80 | 0.015 |

TABLE 22

| Oil | Reaction time (h) | Catalyst/oil (weight %) | FAME (mass %) | Total glycerin (mass %) | Triglyceride (mass %) | Diglyceride (mass %) | Monoglyceride (mass %) | Free glycerin (mass %) |
|---|---|---|---|---|---|---|---|---|
| Jatropha oil | 3 | 15 | 98.4 | 0.19 | 0.054 | 0.045 | 0.66 | 0.010 |
| Palm oil | 3 | 15 | 98.4 | 0.22 | 0.074 | 0.10 | 0.70 | 0.016 |
| Waste food oil | 3 | 15 | 97.6 | 0.15 | 0.062 | 0.10 | 0.49 | 0.0039 |
| PFAD | 5 | 30 | 97.4 | 0.083 | 0.057 | 0.14 | 0.17 | 0.013 |
| Soy oil | 3 | 15 | 98.0 | 0.21 | 0.059 | 0.14 | 0.65 | 0.018 |
| Canola oil | 3 | 15 | 97.8 | 0.18 | 0.045 | 0.064 | 0.60 | 0.016 |

Example 21 and Comparative Example 3

Test for Durability During Biodiesel Fuel Preparation

With the catalyst B, and the reference catalysts R5 and R6, a test for durability during a biodiesel fuel synthesis through transesterification between an oil and methanol was conducted according to the following procedure.

Specifically, 2 g of a catalyst was filled in a stainless-made reaction tube (with an inner diameter of 0.93 mm) and dried under a nitrogen stream at 110° C. for 2 hours. After this, a reaction was induced at a reaction temperature of 180° C., at methanol/jatropha oil (molar ratio) of 100, and at a jatropha oil feeing rate WHSV of 0.5 h$^{-1}$.

Figure 6:
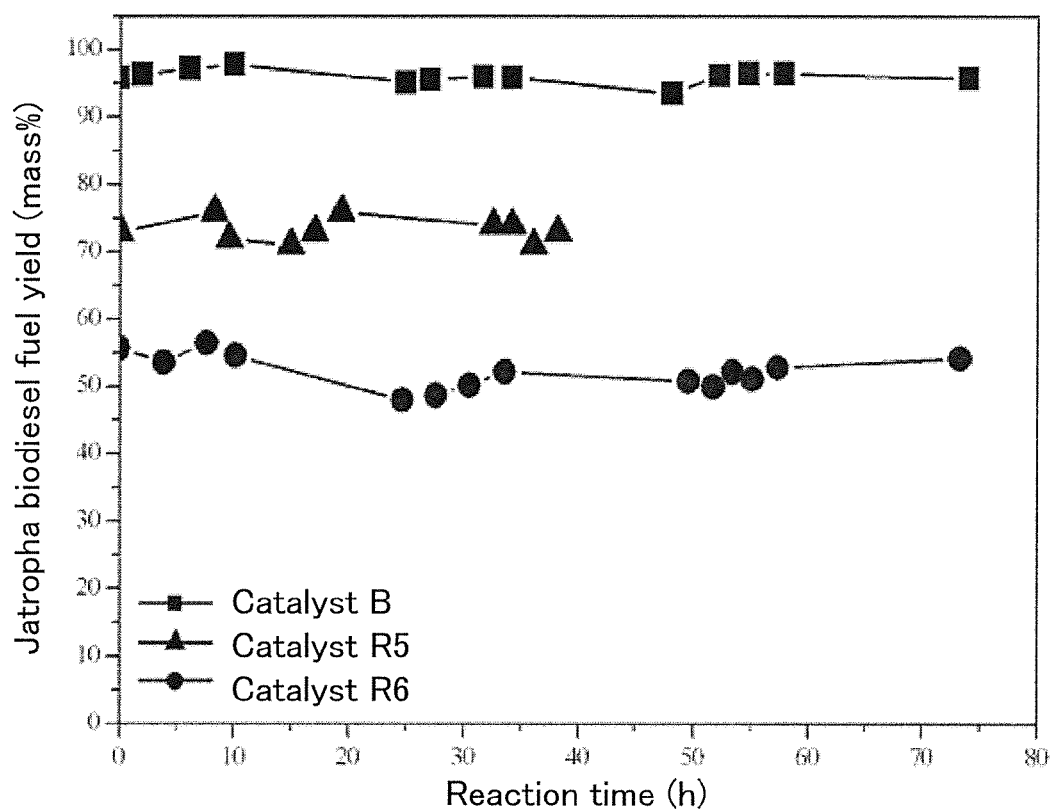
FIG. 6 is a diagram showing durability of a catalyst B and reference catalysts R5 and R6 in preparation of a biodiesel fuel.

FIG. 6 shows the jatropha oil biodiesel fuel yields (% by mass) when the reaction was induced under the conditions described above.

As can be clearly seen from FIG. 6, none of the catalysts showed activity dropping and had durability, but resulted in greatly different biodiesel fuel yields. Only the catalyst B of the present invention satisfied the biodiesel fuel quality standards (i.e., a FAME content should be 96.5% by mass or higher).

What is claimed is:

1. A biodiesel fuel production method, comprising:
    obtaining a fatty acid alkyl ester through a transesterification reaction between an oil and an alcohol in the presence of a transesterification catalyst that comprises a titanium-containing mesoporous silica,
    wherein the titanium-containing mesoporous silica is SBA-15 and has a pore diameter of from 6.5 nm to 8 nm;
    wherein a raw material oil of the biodiesel fuel comprises 1% to 10% of water and fatty acid relative to a total amount of oil in the raw material oil; and
    wherein the biodiesel fuel production method does not comprise a step of removing a water content and a free fatty acid during transesterification; and
    wherein the mesoporous silica has a Ti/Si molar ratio of from 0.03 to 0.07.

2. The biodiesel fuel production method according to claim 1,
    wherein the mesoporous silica has a Ti/Si molar ratio of from 0.03 to 0.05.

3. A biodiesel fuel production method, comprising:
    obtaining a fatty acid alkyl ester through a transesterification reaction between an oil and an alcohol in the presence of a transesterification catalyst that comprises a titanium-containing mesoporous silica,
    wherein the titanium-containing mesoporous silica comprises Ti and Si as skeleton constituent elements, has a mesostructured cellular form (MCF), and has a pore diameter of 5 nm or greater;
    wherein a raw material oil of the biodiesel fuel comprises 1% to 10% of water and fatty acid relative to a total amount of oil in the raw material oil;
    wherein the biodiesel fuel production method does not comprise a step of removing a water content and a free fatty acid during transesterification; and
    wherein the catalyst has pore diameter of from 15 nm to 40 nm.

4. The biodiesel fuel production method according to claim 3, wherein the mesoporous silica has a Ti/Si molar ratio of from 0.03 to 0.07.

5. The biodiesel fuel production method according to claim 1, wherein the mesoporous silica has an amorphous structure.

6. The biodiesel fuel production method according to claim 3, wherein the mesoporous silica has an amorphous structure.

* * * * *